(12) United States Patent
Cansell et al.

(10) Patent No.: US 6,671,546 B2
(45) Date of Patent: *Dec. 30, 2003

(54) IMPULSES OR A SERIES OF IMPULSES FOR DEFIBRILLATION AND DEVICE TO GENERATE THEM

(75) Inventors: Albert Cansell, Wissembourg (FR); Ivan Daskalov, Sofia (BG)

(73) Assignee: Schiller Medical, Wissembourg (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/290,532

(22) Filed: Nov. 8, 2002

(65) Prior Publication Data

US 2003/0078622 A1 Apr. 24, 2003

Related U.S. Application Data

(63) Continuation of application No. 09/492,348, filed on Jan. 27, 2000, now Pat. No. 6,493,580.

(30) Foreign Application Priority Data

Jan. 27, 1999 (FR) .............................................. 99 00989

(51) Int. Cl.[7] ................................................. A61N 1/18
(52) U.S. Cl. ............................................. 607/5; 607/71
(58) Field of Search ............................ 607/5–8, 14–15, 607/16–17, 68, 70, 69, 72, 74

(56) References Cited

U.S. PATENT DOCUMENTS

| | | | |
|---|---|---|---|
| 4,037,164 A | * | 7/1977 | Pickton et al. ............... 327/178 |
| 4,222,386 A | | 9/1980 | Smolnikov et al. |
| 4,566,457 A | | 1/1986 | Stemple |
| 5,601,608 A | * | 2/1997 | Mouchawar .................... 607/5 |
| 5,827,326 A | * | 10/1998 | Kroll et al. ..................... 607/5 |
| 6,096,063 A | * | 8/2000 | Lopin et al. .................... 607/8 |
| 6,298,266 B1 | | 10/2001 | Rubin et al. |
| 6,353,758 B1 | | 3/2002 | Gliner et al. |

FOREIGN PATENT DOCUMENTS

| | | |
|---|---|---|
| EP | 0 515 059 | 11/1992 |
| GB | 2 190 296 | 11/1987 |
| WO | 97 38753 | 10/1997 |
| WO | 98 26841 | 6/1998 |

* cited by examiner

Primary Examiner—Mark Bockelman
(74) Attorney, Agent, or Firm—Young & Thompson

(57) ABSTRACT

A series of defibrillation impulses and device for generating them in which the impulses are constituted by a wave with at least two phases of which successive phases of opposite polarity are cut or chopped at a higher frequency than the frequency of the successive phases.

19 Claims, 6 Drawing Sheets

IMPULSES OR A SERIES OF IMPULSES FOR DEFIBRILLATION AND DEVICE TO GENERATE THEM

The present invention relates to the medical field, more particularly to cardiac defibrillation, and particular to external or transthoracic defibrillation and internal defibrillation, as well as the implantable defibrillator, and has for its object new impulses or series of defibrillation impulses, as well as a device to generate or produce these latter.

At present, the great majority of defibrillations are carried out by means of a positive monophase impulse resulting generally in the discharge of a capacitor through the patient and, as the case may be, an inductance.

However, numerous forms of impulses are possible (see for example: A. Cansell, La Revue des Samu; 1997-5, 229 to 237).

It has been particularly proposed recently to interrupt the discharge of the capacitor, then to modify the connection to end the discharge with a reversed polarity, so as to supply impulses in the form of a biphase wave.

This manner of biphase defibrillation has been described in numerous works, particularly for example in the document WO 95/05215. The same principle of biphase defibrillation (with two or more phases of opposite polarity) is however older, because the first defibrillations were carried out by Prevost and Batelli by means of a sinusoidal AC current of 45 Hz (CR Acad. Sci. 1899; 129:1267). Similarly, all the defibrillations used in the former USSR used and still use an oscillating capacitor discharge, comprising two to three alternate phases (Negovsky et al., Resuscitation 1980; 8:53–67).

Moreover, it has also been proposed to use, to excite the cardiac cells, series of rectangular impulses of the same polarity delivered at high frequency and delimited by a monophase rectangular envelope, so as to obtain a pulsed monophase wave of rectangular form and chopped by a high frequency signal (Janice L. Jones et al., "Cellular excitation with high-frequency chopped defibrillator waveforms", Proc. IEEE, p. 17 et 18, 6/1994).

However, these different types of known defibrillation impulses all have, either because of their nature, or because of the mode of embodying the devices generating them, limitations and drawbacks such as for example limited available energy, great difficulty of practical embodiment, limited efficiency for a given available energy or else a risk of harm to the patient.

Moreover, there continuously exists the need, given their critical character, of improving the efficiency of defibrillation techniques, particularly to reduce the quantity of energy delivered by them to the patient whilst guaranteeing a success rate greater than that obtained by present techniques.

The present invention particularly has for its object to overcome certain of the drawbacks and limitations mentioned above and to fulfill the mentioned need.

However, the inventors have determined, in a surprising and unforeseeable manner, that the impulses or series of defibrillation impulses constituted by a wave with at least two phases whose successive phases of opposite polarity are cut or chopped at a higher frequency than the frequency of said successive phases, will permit overcoming at least certain of the drawbacks and limitations mentioned above and will have a defibrillation efficiency substantially greater than the existing shapes of defibrillation waves.

The invention will be better understood from the following description, which relates to preferred embodiments, given by way of non-limiting examples, and explained with reference to the accompanying schematic drawings, in which.

Figure 1A:
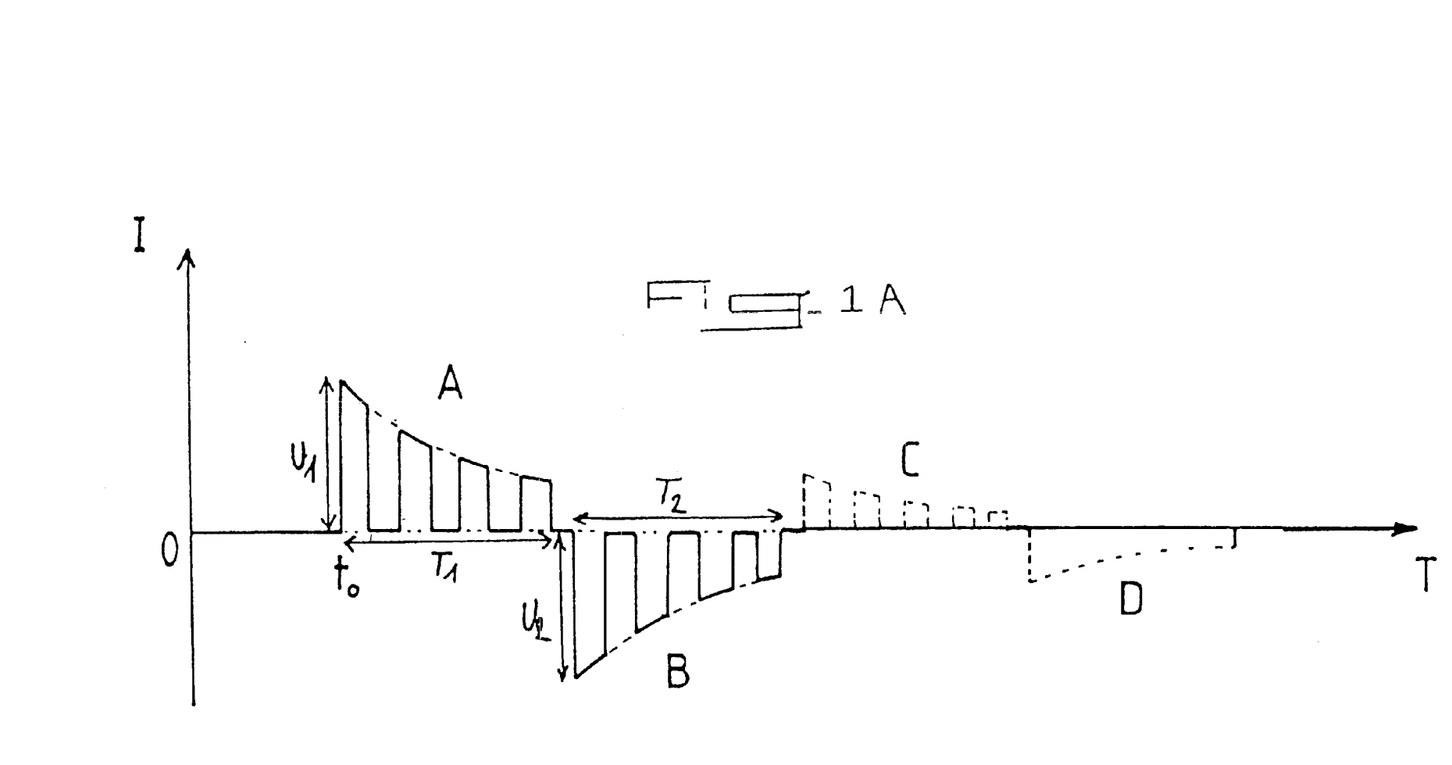
FIG. 1A is a curve of intensity/time representing a series of impulses according to the invention, according to one embodiment of this latter, comprising two, three or four successive phases A, B, C and D.
Figure 1B:
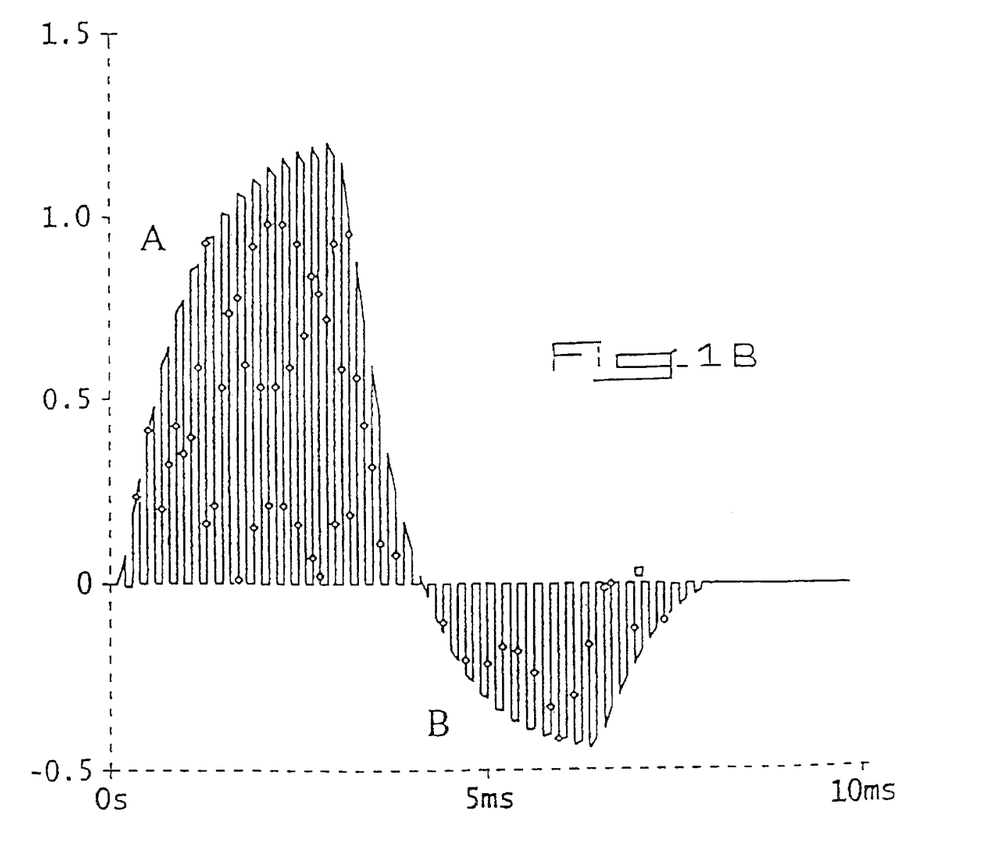
FIG. 1B is a curve of intensity/time representing a series of impulses according to the invention, according to another embodiment of this latter, comprising two successive phases A and B.

As is shown in FIG. 1 of the accompanying drawings, the impulses or the series of defibrillation impulses is or are constituted by an at least biphase wave whose successive phases of opposite polarity are cut or chopped at a higher frequency than the frequency of said successive phases.

There are thus obtained successive defibrillation impulses, of opposite phase, each comprised by a set of elementary impulses, individual and separate, which are all delimited by and comprised within the envelope formed by the at least biphase wave. The frequency of occurrence and the duration of the separate elementary impulses are defined by the cutting or chopping signal altering the continuous phases of said wave, so as to form phases comprising successive pulsed defibrillation impulse chains.

This series of impulses is preferably constituted by two, (for example A and B), three (for example A, B and C) or if desired four (for example A, B, C and D) consecutive alternating phases (see as a non-limiting example the impulse series shown in FIGS. 1A and 1B).

It will be noted that it is possible easily to vary the energy of defibrillation applied to the patient, no matter what the energy of the unaltered multiphase wave or the energy stored for defibrillation, by varying the factor of the cutting or chopping signal form of said wave.

Preferably, the cutting or chopping frequency is at least four times greater than the frequency of the multiphase wave.

According to one characteristic of the invention, the duration of each phase is comprised between 2 ms and 8 ms, preferably between 3 ms and 5 ms, the cutting or chopping frequency thus being greater than 500 Hz.

In practice, a chopping frequency is preferably greater than about 1 KHz and less than about 30 KHz, preferably less than about 10 KHz, the chopping frequencies greater than 10 KHz, and up to 30 KHz, not permitting obtaining fully the preferable properties of the invention.

According to one embodiment of the invention, corresponding in particular to the use of discharges from capacitors for the generation of defibrillation impulses, the envelope or wave forming the envelope of the various phases is present in the form of a truncated curve, for example in the form of a truncated exponential (FIG. 1A).

According to another embodiment of the invention, the envelope or wave forming an envelope of the different successive phases can preferably be present in a rounded form, biphase and asymmetrical (see for example FIG. 1B of the accompanying drawings).

In this second embodiment of the invention, the wave forming envelope could be obtained, for example, by means of a discharge of a capacitor in an oscillating regime (RLC circuit), a capacitor discharge through a low-pass filter (FIG. 1B) or else a function generator delivering a signal of desired shape.

However, instead of proceeding by chopping the discharges or signals of very high voltage, delivered for example by the capacitors, the defibrillation impulses according to the invention can also be produced at the secondaries of the transformers amplifying a chopped or pulsed signal at least biphasic, generated at the primary, which permits generating any desired wave form.

Moreover, the inventors have discovered that it is possible further to improve the efficiency of the defibrillation impulses according to the invention, by providing that the wave amplitude at the beginning of the second phase be greater or less than the amplitude of the wave at the end of the first phase, particularly in the case of truncated waves, if desired as a function of thoracic impedance.

This adjustment of the amplitude of the wave at the beginning of the second phase can be obtained by using for example two separate capacitors to generate respectively the first and second phase.

Further experimentation and evaluation of the overall characteristics described above have led to a practical realization, giving particularly interesting results. This particular realization is described in greater detail, by way of non-limiting example, hereafter.

An impulse or series of defibrillation impulses constituted by a wave comprising two consecutive alternate phases of opposite polarities, is produced, each of these phases being obtained by means of the discharge of a capacitor, each of these capacitors (C1 and C2) having a capacitance of 30 $\mu$F and each of these phases being moreover cut or chopped at a frequency of 5 kHz.

The first of these phases has at its beginning a reference voltage U1 and the second phase has at its beginning a voltage U2 whose value is comprised between about $\frac{1}{3}$ and $\frac{2}{3}$ of the value of U1, each of these phases having a duration T1 and T2 of about 4 ms.

The reference voltage U1 being variable and determining the impulse energy, as well as the charge and the current through the patient, whose values should be-an impulse to be capable of defibrillating, greater than a threshold, called a defibrillation threshold.

However, given that the patients, as well as the patient-electrode interface, should have a thoracic impedance Z which varies strongly from one case to the next (between about 30 ohms and 150 ohms)—which will modify the slope of the exponential discharges which constitute the envelopes of the two phases as well as the energy, the mean current through the patient, the electrical charge delivered and precisely the efficiency of defibrillation-the inventors have sought a means to take account of these thoracic impedance variations by measuring it in the course of the defibrillation shock and by acting on the duration of each of the impulses or phases, or, as the case may be, on only of the two, to seek to compensate these variations of characteristics and efficiency.

The measurement of the thoracic impedance is carried out by measuring the voltage of the terminals of the patient by means of successive measurements carried out about every 500 $\mu$s (at the instants at which the current is present) and by calculating for each pair of successive points, the corresponding resistance, knowing the value of the capacitor supplying the impulse.

Knowing the thoracic impedance Z, one can act on the duration of each phase. To do that, if we take the example of the preferred embodiment above, the solution provided by the inventors to render the values T1 and T2 variable and adjustable as a function of Z (the impedance of the patient himself plus the impedance of the patient/defibrillation electrodes interface) consists first in associating the value of 4 ms used above for T1 and T2, with a mean value of Z of about 80 ohms.

If Z has a lower value than 80 ohms for one of the phases or both of them, then T1 and/or T2 will be decreased, without at the same time falling below a value of 3 ms, so as not to fall below the lower limit imposed by the time constant of the myocardial cell.

If Z has a value greater than 80 ohms for one of the phases or both of them, then T1 and/or T2 will be increased, without however exceeding a value of 5 ms so as not to go beyond the upper limit imposed by the time constant of the myocardial cell.

It is important to note that this regulation of the duration of the first and/or second phase or impulse as a function of the value of the thoracic impedance Z measured in the course of defibrillation, does not consist in a simple compensation to have constant energy, but in a regulation of the impulse parameters or defibrillation phases to remain within optimum range of their characteristics according to the physiological plan.

The following table indicates the approximate values found as effective for such a regulation of T1 and T2 as a function of Z:

| Z in ohms | T1 or T2 in ms |
| --- | --- |
| 30 | 3 |
| 40 | 3 |
| 60 | 3.5 |
| 80 | 4 |
| 100 | 4.5 |
| 120 | 5 |
| 150 | 5 |

It should be noted that the values are given only by way of example and are not limiting, and are based on the results of experiments the inventors carried out until now.

The arrangements for adjusting and regulating described above, could of course also be applied in the field of defibrillation processes with other structures of defibrillation devices, for example of the type comprising only a single capacitor in lieu of the two capacitors C1 and C2 for energy storage, or uncut biphase waves.

The present invention also has for its object a device for generating defibrillation impulses of the type described above, forming a constituent part of a defibrillator.

Figure 2:
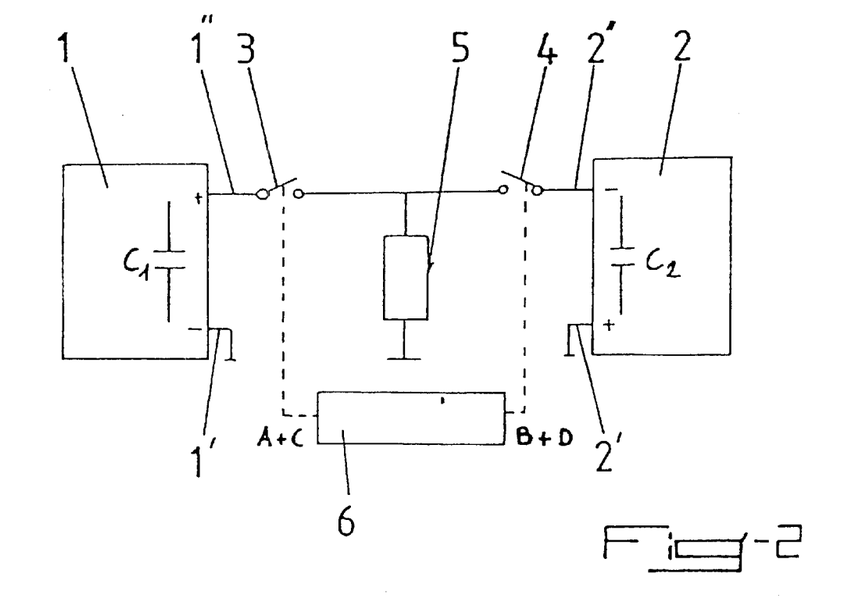
FIGS. 2 and 3 are simplified schematic representations of two modified embodiments of an impulse generating device according to a first embodiment of the invention.
Figure 3:
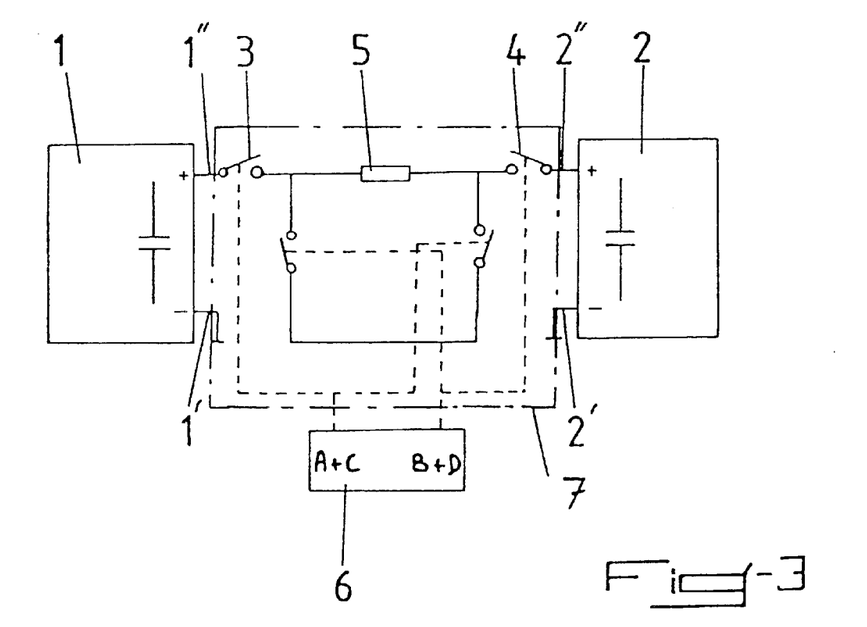
Figure 6:
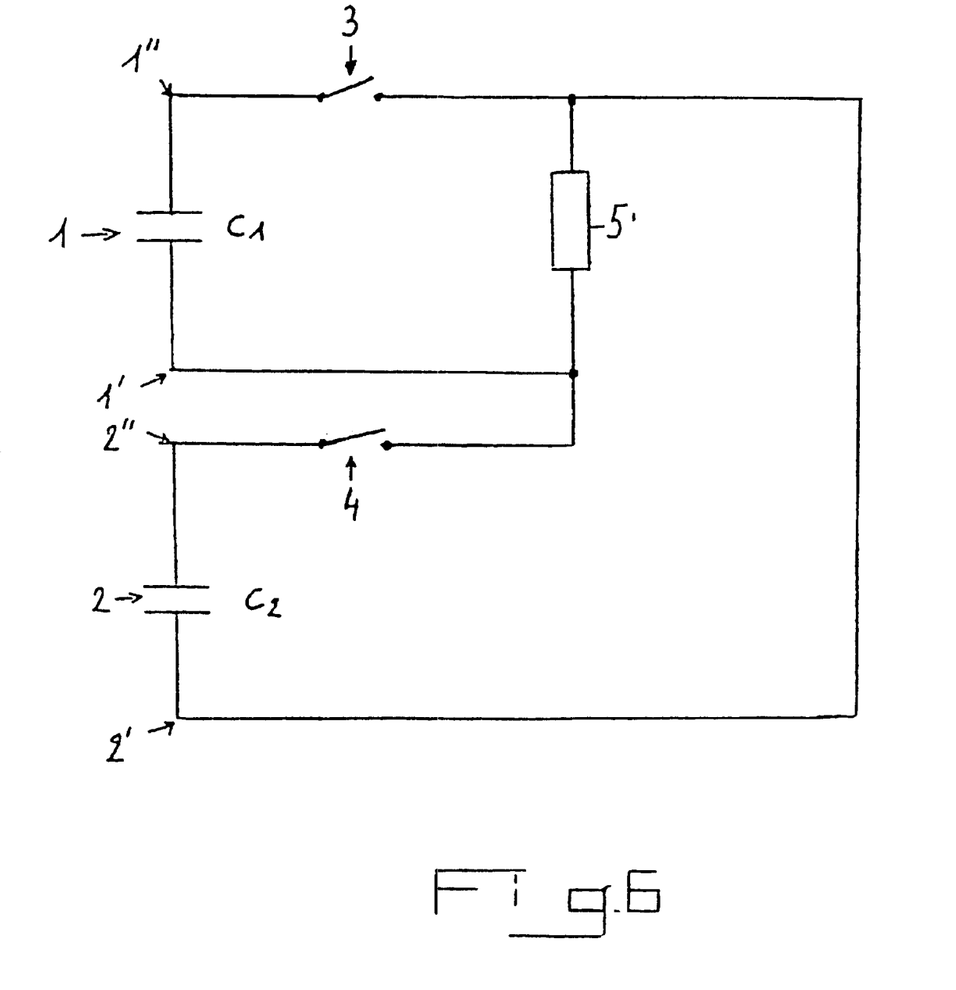

As shown in FIGS. 2, 3 and 6 of the accompanying drawings, said device can be essentially constituted, on the one hand, by two capacitors 1 and 2, having are not two common terminals 1' and 2 ' or connected together, adapted to store electrical energy of defibrillation, and, on the other hand, by at least two switches or commutators 3 and 4 controlled by a control circuit 6, each ensuring the alternate connection of the other terminal or of one 1", 2" of the terminals of each of the two capacitors 1 and 2 with the patient 5 and actuated successively so as to produce partial discharges of the respective capacitors in question, 1 and 2, generating a series of pulses in the form of an at least biphase wave whose successive phases of opposite polarity are cut or chopped at a higher frequency than the frequency of said successive phases.

According to a first modification of the invention, shown in FIG. 2 of the accompanying drawings, the terminals 1" and 2" of the capacitors 1 and 2 discharge alternately and have opposite polarities.

According to a second modification of the invention, shown in FIG. 3 of the accompanying drawings, the terminals 1" and 2" of the capacitors 1 and 2 discharge alternately, having identical polarities, the resulting impulses being applied to the patient 5 through a bridge mounting 7 that can deliver impulses of opposite phases.

The capacitors 1 and 2 could either have a common point, or they can be completely separate and independent as a function of the envisaged use and of the construction of each apparatus or defibrillator device.

Figure 5:
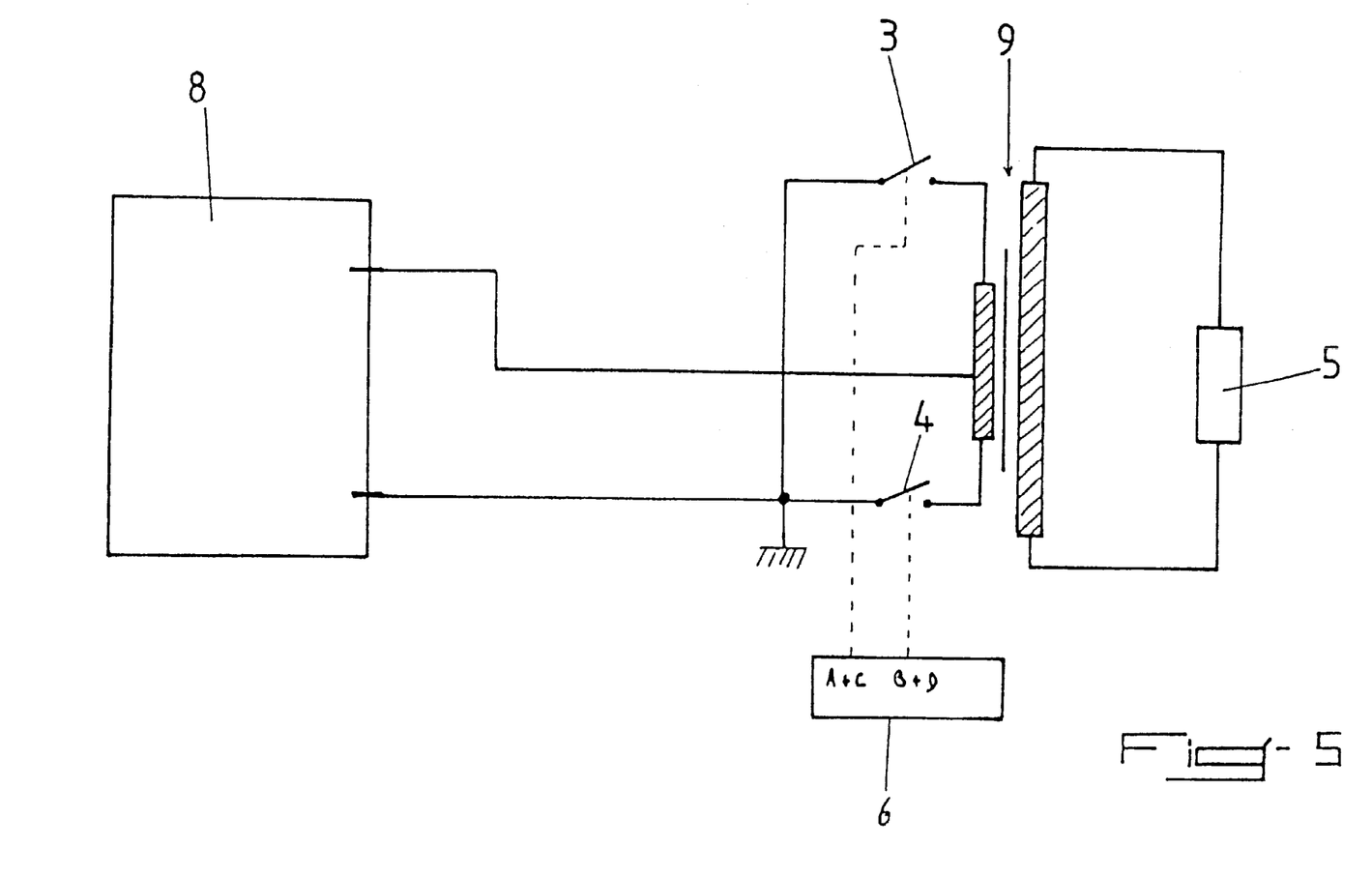
FIG. 5 is a simplified schematic representation of a second embodiment of a device for generating impulses according to the invention, and, FIG. 6 is a simplified schematic representation of another modified embodiment of a device for generating impulses according to the invention.

According to another embodiment of the invention, shown in FIG. 5 of the accompanying drawings and permitting particularly producing various wave forms or envelopes, the device for generating defibrillation impulses of the type mentioned above can be principally constituted by a low voltage wave generator 8 connected by means of the primary of a tension boosting transformer 9 whose secondary is connected to the patient 5, the two ends of said primary being adapted to be alternatively connected to the ground by means of switches or of commutators 3 and 4.

As shown in FIGS. 2 to 5 of the accompanying drawings, the chopping of the wave is carried out by the action of switches or commutators 3 and 4 by means of a crenelated signal whose frequency and shape factor is preferably variable, delivered by a control circuit 6 embodying a corresponding signal generator, clock circuits or the like.

Switches 3 and 4 ensure a function of chopping and inversion.

Figure 4:
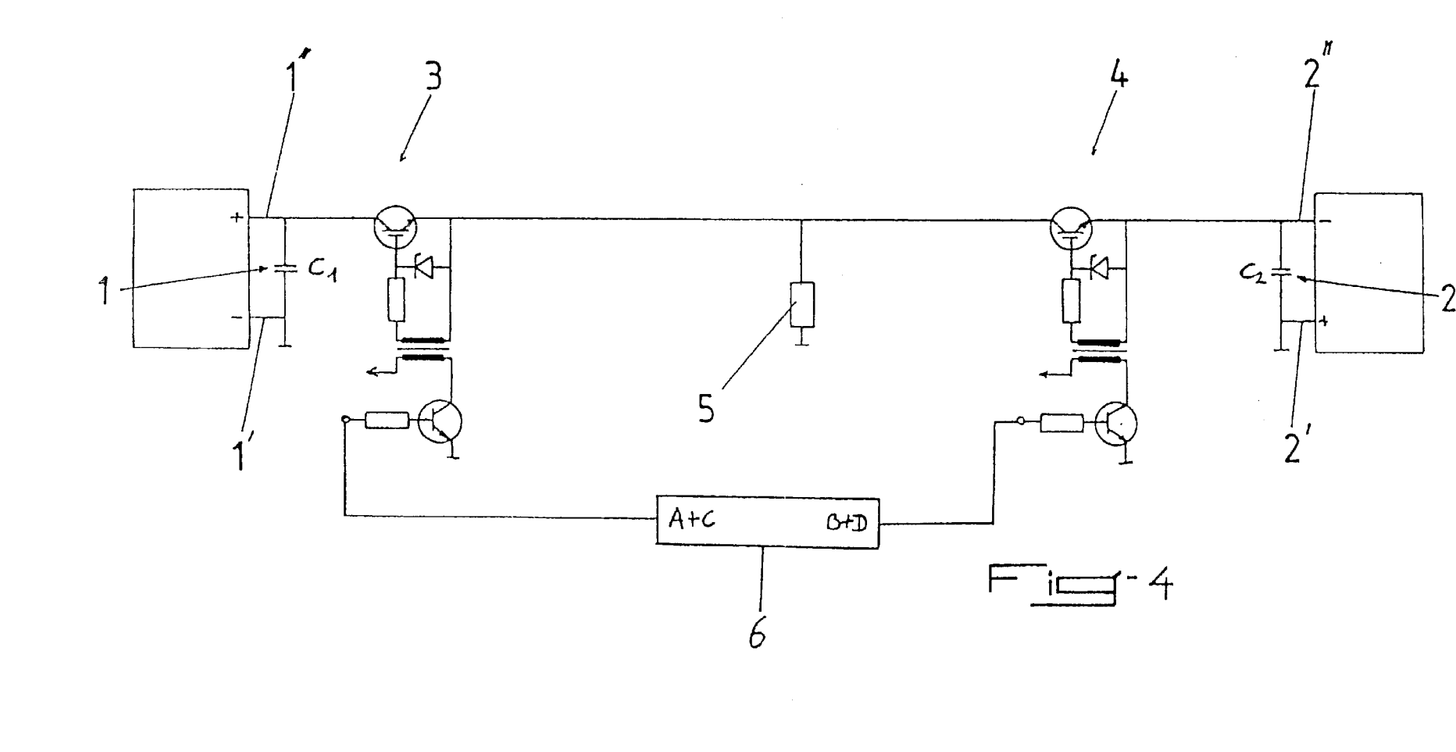
FIG. 4 is a simplified representation, but more detailed, of the device shown in FIG. 2, showing particularly a possible embodiment of the switches used.

As shown in FIG. 4 of the accompanying drawings, the switches 3 and 4 could for example each be constituted by a transistor circuit known by the designation IGBT, or by several circuits of this type mounted in series and/or in parallel, as a function of the charge voltages of the capacitors 1 and 2 and of the maximum voltages and currents of the defibrillation impulses applied to the patient.

The generation device also will have, as the case may be, the means necessary to carry out the thoracic impedance measurement in the course of defibrillation and to correspondingly regulate the discharges of the condensers 1 and 2 and/or the durations of the successive phases.

The experimental defibrillation results produced by the inventors on animals, by means of different forms of defibrillation impulses described above, are set forth in the following table.

For the conventional monophase impulse form, there is used a reference energy of the value 100 necessary and sufficient to obtain effective defibrillation. The other forms of impulse are given in relative values, relative to the value of the mentioned reference, also necessary and sufficient to carry out effective defibrillation.

| | |
|---|---|
| Monophase wave | 100 |
| Biphase wave (uncut) | 65 |
| Biphase wave cut at 5 KHz according to the present invention | 30 to 40 |

It will thus be seen, on the basis of the above results, that a defibrillation process, particularly transthoracic, applied to humans and using impulses or series of impulses according to the present invention, for example delivered by a device such as described above, will have, relative to the known processes, a similar improvement.

Similarly, the advantages of reducing the energy obtained in the particular application of external defibrillation, whose results are described above, can also be observed in similar proportion in the case of internal defibrillation and of the implantable defibrillator, using the principles of the present invention.

Of course, the invention is not limited to the embodiments described and shown in the accompanying drawings. Modifications remain possible, particularly as to the construction of the various elements or by substitution of technical equivalents, without thereby departing from the scope of protection of the invention.

What is claimed is:

1. A process for generating a defibrillating signal with at least two successive phases, the method comprising the steps of:

charging at least one capacitor and discharging the at least one capacitor in a patient as a defibrillating signal with at least two successive phases, each of the successive phases consisting of a series of individual defibrillating impulses formed by a cutting or chopping signal while switching each of the impulses between zero output and a defibrillating output at a frequency higher than a frequency of the successive phases; and varying a form of the cutting or chopping signal.

2. The process for generating a defibrillating signal according to claim 1, whereas the defibrillation energy discharged to the patient is set by the step of varying the form of the cutting or chopping signal.

3. The process of claim 1, wherein the successive phases have alternating polarities.

4. The process of claim 3, wherein there are at least three of the successive phases.

5. The process of claim 1, wherein the frequency of the switching between the zero and defibrillating outputs is at least four times greater than the frequency of the successive phases.

6. The process of claim 1, wherein a duration of each of the successive phases is 2 ms to 8 ms, and the frequency of the switching between the zero and defibrillating outputs is greater than 500 Hz.

7. The process of claim 6, wherein the frequency of the switching between the zero and defibrillating outputs is greater than about 1 KHz and less than about 30 KHz.

8. The process of claim 1, wherein the defibrillation output has a form of a truncated curve.

9. The process of claim 1, wherein an amplitude of the defibrillation output at a start of a second one of the phases is greater than an amplitude of the defibrillation output at an end of a first one of the phases immediately preceding the second one of the phases.

10. The process of claim 1, wherein an amplitude of the defibrillation output at an end of a first one of the phases is greater than an amplitude of the defibrillation output at a start of a second one of the phases immediately following the first one of the phases.

11. The process of claim 1, wherein an amplitude of the defibrillation output at a start of a second one of the phases is between one-third and two-thirds of an amplitude of the defibrillation output at a start of a first one the phases immediately preceding the second one of the phases.

12. The process of claim 1, further comprising the steps of measuring thoracic impedance and controlling a duration of each of the successive phases varies as a function of the thoracic impedance.

13. A device for generating a defibrillation signal having plural successive phases of opposite polarities, the device comprising at least one capacitor for storing defibrillation energy;

switching means for discharging said at least one capacitor to provide a defibrillation signal with plural successive phases, each of the successive phases consisting of a series of individual defibrillating impulses switching between zero output and defibrillation output at a frequency higher than the frequency of the successive phases.

14. The device according to claim 13, whereas said defibrillation signal is formed by a cutting or chopping signal and whereas said device comprises means for varying the factor of form of said cutting or chopping signal.

15. The device according to claim 14, whereby the energy discharged to the patient is variable by varying the factor of form of said cutting or chopping signal.

16. The device according to claim 13, the device comprising two capacitors that store defibrillation energy whereas the switching means for discharging said two capacitors are designed to provide a defibrillation signal with plural successive phases with alternating polarities.

17. The device of claim 13, wherein said switching means comprises two switches controlled by a control circuit and are each connected to a respective one of said two capacitors.

18. The device of claim 13, wherein said two switches are connected to terminals of said respective two capacitors that have opposite polarities.

19. The device of claim 13, wherein said two switches are connected to terminals of said respective two capacitors that have the same polarity, the device further comprising a bridge that converts a polarity of alternating ones of the successive phases.

* * * * *